(12) United States Patent
Sakuma et al.

(10) Patent No.: US 11,348,244 B2
(45) Date of Patent: May 31, 2022

(54) MEDICAL IMAGE PROCESSING APPARATUS, MEDICAL IMAGE PROCESSING METHOD AND STORAGE MEDIUM

(71) Applicants: The University of Tokyo, Bunkyo-ku (JP); CANON MEDICAL SYSTEMS CORPORATION, Otawara (JP)

(72) Inventors: Ichiro Sakuma, Bunkyo-ku (JP); Minoru Ono, Bunkyo-ku (JP); Eriko Maeda, Bunkyo-ku (JP); Kan Nawata, Bunkyo-ku (JP); Haruo Yamauchi, Bunkyo-ku (JP); Hiroyuki Tsukihara, Bunkyo-ku (JP); Kenji Ino, Bunkyo-ku (JP); Fumimasa Shige, Otawara (JP); Katsuhiko Fujimoto, Saitama (JP); Takuya Sakaguchi, Utsunomiya (JP)

(73) Assignees: The University of Tokyo, Bunkyo-ku (JP); CANON MEDICAL SYSTEMS CORPORATION, Otawara (JP)

( * ) Notice: Subject to any disclaimer, the term of this patent is extended or adjusted under 35 U.S.C. 154(b) by 3 days.

(21) Appl. No.: 16/835,840

(22) Filed: Mar. 31, 2020

(65) Prior Publication Data
US 2020/0311941 A1    Oct. 1, 2020

(30) Foreign Application Priority Data

Apr. 1, 2019    (JP) .............................. JP2019-069641

(51) Int. Cl.
*G06T 7/00*    (2017.01)
*G06T 7/73*    (2017.01)
(Continued)

(52) U.S. Cl.
CPC .............. *G06T 7/0016* (2013.01); *G06T 7/74* (2017.01); *G16H 20/40* (2018.01); *G16H 30/40* (2018.01);
(Continued)

(58) Field of Classification Search
CPC ... G06T 7/0012; G06T 7/0014; G06T 7/0016; G06T 7/60; G06T 7/70; G06T 7/73;
(Continued)

(56) References Cited

U.S. PATENT DOCUMENTS

| 2007/0014452 A1 | 1/2007 | Suresh et al. ................. 382/128 |
| 2008/0317195 A1 | 12/2008 | Kobayashi et al. ............. 378/4 |

(Continued)

FOREIGN PATENT DOCUMENTS

| JP | 2009-022733 A | 2/2009 |
| JP | 2014-108313 A | 6/2014 |

(Continued)

OTHER PUBLICATIONS

Nakao et al., "Vertex-Preserving Cutting Methods for Deformable Elastic Models", The Virtual Reality Society of Japan, vol. 12, No. 4, 2007, 16 pages(with English Abstract & Partial English Translation).

(Continued)

*Primary Examiner* — Andrew W Johns
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to obtain feature values related to the shape and a property of the heart. The processing circuitry is configured to estimate, by using the feature values, a state of the heart after a chest is opened. The processing circuitry is configured to estimate, based on a result of the estimation (Continued)

of the state of the heart, a state of the heart after the chest is closed after a treatment is completed. The processing circuitry is configured to output a parameter related to the estimated state of the heart after the chest is closed to a display.

14 Claims, 9 Drawing Sheets

(51) Int. Cl.
  *G16H 20/40* (2018.01)
  *G16H 50/30* (2018.01)
  *G16H 30/40* (2018.01)

(52) U.S. Cl.
  CPC ... *G16H 50/30* (2018.01); *G06T 2207/10081* (2013.01); *G06T 2207/10088* (2013.01); *G06T 2207/10132* (2013.01); *G06T 2207/30048* (2013.01)

(58) Field of Classification Search
  CPC ........... G06T 7/74; G06T 17/00; G06T 19/00; G06T 2207/30048; G16H 20/40; G16H 30/40; G16H 50/30; A61B 34/10; A61B 2034/101; A61B 2034/104; A61B 2034/105
  See application file for complete search history.

(56) References Cited

U.S. PATENT DOCUMENTS

| | | | |
|---|---|---|---|
| 2014/0316758 A1 | 10/2014 | Yagi et al. | .......... G06F 17/5009 |
| 2014/0343906 A1 | 11/2014 | Yagi et al. | .......... G06F 19/3437 |
| 2015/0032435 A1 | 1/2015 | Yagi et al. | .......... G06F 19/3437 |
| 2015/0127031 A1 | 5/2015 | Yagi et al. | .............. A61B 19/50 |
| 2015/0127316 A1 | 5/2015 | Avisar | .................... A61B 19/50 |
| 2018/0098814 A1 | 4/2018 | Avisar | .................... A61B 34/10 |

FOREIGN PATENT DOCUMENTS

| | | |
|---|---|---|
| JP | 2014-522248 A | 9/2014 |
| WO | WO 2012/135653 A1 | 10/2012 |
| WO | WO 2013/031742 A1 | 3/2013 |

OTHER PUBLICATIONS

Extended European Search Report dated Aug. 26, 2020 in European Patent Application No. 20167334.0, 10 pages.

Yonghoon Rim, et al., "Personalized Computational Modeling of Mitral Valve Prolapse: Virtual Leaflet Resection," PLoS ONE, vol. 10, No. 6, XP055722519, Jun. 23, 2015, pp. 1-15.

FIG.4
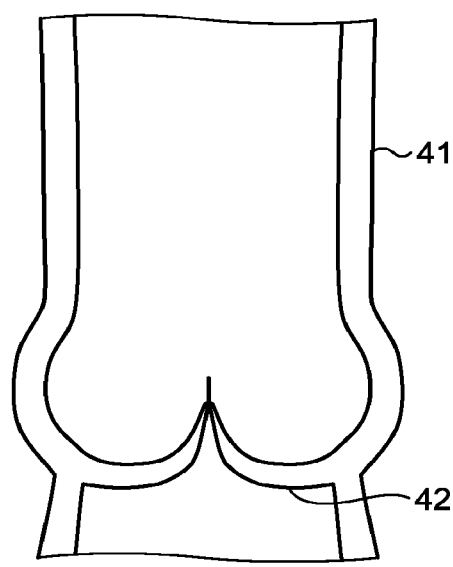
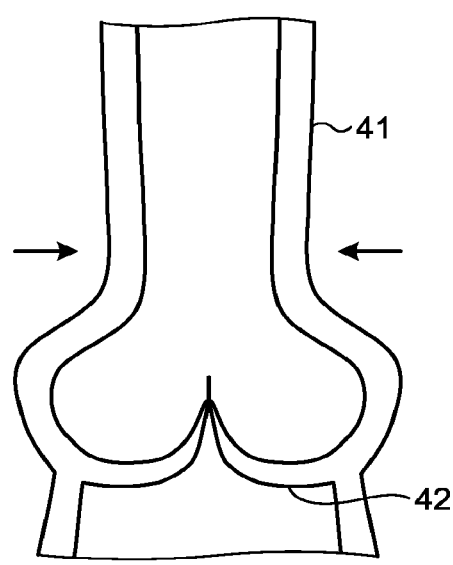

MEDICAL IMAGE PROCESSING APPARATUS, MEDICAL IMAGE PROCESSING METHOD AND STORAGE MEDIUM

CROSS-REFERENCE TO RELATED APPLICATIONS

This application is based upon and claims the benefit of priority from Japanese Patent Application No. 2019-069641, filed on Apr. 1, 2019; the entire contents of which are incorporated herein by reference.

FIELD

Embodiments described herein relate generally to a medical image processing apparatus, a medical image processing method and a storage medium.

BACKGROUND

Conventionally, as techniques for assisting surgery on the heart, techniques have been known by which surgery on the heart is simulated by using image data acquired by a medical image diagnosis apparatus. As an example of such techniques, a technique is known by which, before surgery to open the chest, an optimal suture position is simulated for the surgery to join a heart valve and a valve base part with a graft (an artificial blood vessel). However, none of the conventional techniques takes into account deformations of the heart caused by opening and closing the chest. Accordingly, there are some situations where it is difficult to properly assist the surgery performed on the heart.

BRIEF DESCRIPTION OF THE DRAWINGS

FIG. 4 is a drawing illustrating an example of a simulation of a state after the chest is opened that is performed by the estimating function according to the present embodiment;

DETAILED DESCRIPTION

A medical image processing apparatus according to an embodiment includes an obtaining unit, an estimating unit, and an output unit. The obtaining unit is configured to obtain feature values related to the shape and a property of the heart. The estimating unit is configured to estimate, by using the feature values, a state of the heart after a chest is opened and estimate, based on a result of the estimation of the state of the heart, a state of the heart after the chest is closed after a treatment is completed. The output unit is configured to output a parameter related to the estimated state of the heart after the chest is closed to a display.

In the following sections, exemplary embodiments of a medical image processing apparatus and a medical image processing program will be explained in detail, with reference to the accompanying drawings.

Figure 1:
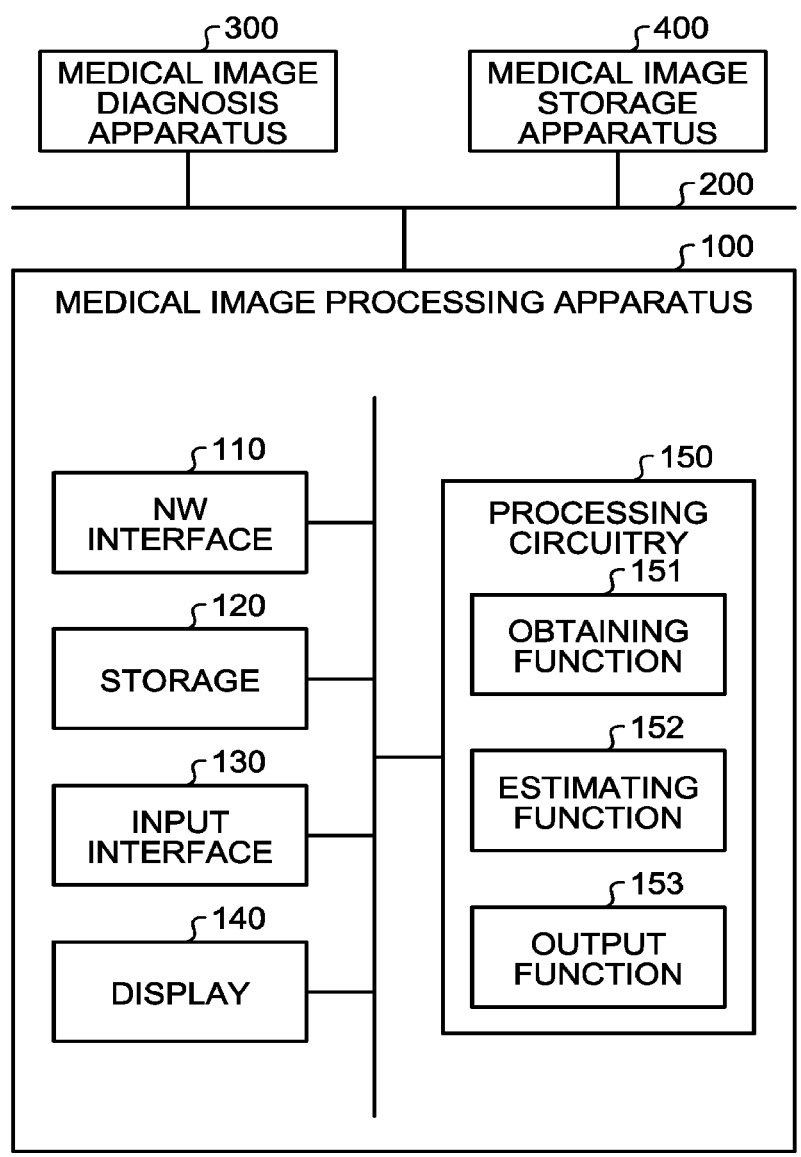
FIG. 1 is a diagram illustrating an exemplary configuration of a medical image processing apparatus according to an embodiment of the present disclosure.

FIG. 1 is a diagram illustrating an exemplary configuration of a medical image processing apparatus according to an embodiment of the present disclosure.

For example, as illustrated in FIG. 1, a medical image processing apparatus 100 according to the present embodiment is connected to a medical image diagnosis apparatus 300 and to a medical image storage apparatus 400 via a network 200 so as to be able to communicate with each other.

The medical image diagnosis apparatus 300 is configured to obtain a medical image of an examined subject (hereinafter "patient") to be used for an image diagnosis process or the like. More specifically, as the medical image, the medical image diagnosis apparatus 300 generates two-dimensional image data or three-dimensional image data (which may be referred to as "volume data") of the patient. For example, the medical image diagnosis apparatus 300 may be an X-ray Computed Tomography (CT) apparatus, a Magnetic Resonance Imaging (MRI) apparatus, an ultrasound diagnosis apparatus, or the like.

The medical image storage apparatus 400 is configured to obtain the image data from the medical image diagnosis apparatus 300 via the network 200 and to store the obtained image data into storage provided on the inside thereof. For example, the medical image storage apparatus 400 is realized by using a computer device such as a server, a workstation, or the like.

The medical image processing apparatus 100 is configured to obtain the image data from the medical image diagnosis apparatus 300 or from the medical image storage apparatus 400 via the network 200 and to perform various types of image processing processes on the obtained image data. For example, the medical image processing apparatus 100 is realized by using a computer device such as a server, a workstation, a personal computer, a tablet terminal, or the like.

More specifically, the medical image processing apparatus 100 includes a network (NW) interface 110, storage 120, an input interface 130, a display 140, and processing circuitry 150.

The NW interface 110 is configured to control transfer and communication of various types of data transmitted and received between the medical image processing apparatus 100 and other apparatuses connected via the network 200. More specifically, the NW interface 110 is connected to the processing circuitry 150 and is configured to output the image data received from the medical image diagnosis apparatus 300 or the medical image storage apparatus 400, to the processing circuitry 150. For example, the NW interface 110 is realized by using a network card, a network adaptor, a Network Interface Controller (NIC), or the like.

The storage 120 is configured to store various types of data therein. More specifically, the storage 120 is connected to the processing circuitry 150 and is configured to store therein image data input thereto and to output the stored image data to the processing circuitry 150, according to instructions sent from the processing circuitry 150. For example, the storage 120 is realized by using a semiconductor memory element such as a Random Access Memory (RAM) or a flash memory, or a hard disk, an optical disk, or the like. The storage 120 is an example of a storage unit.

The input interface 130 is configured to receive input operations of various types of instructions and various types of information from an operator. More specifically, the input interface 130 is connected to the processing circuitry 150 and is configured to convert the input operations received from the operator into electrical signals and to output the electrical signals to a control circuit. For example, the input interface 130 is realized by using a trackball used for setting a Region Of Interest (ROI) or the like, a switch button, a mouse, a keyboard, a touchpad on which an input operation is performed by touching the operation surface thereof, a touch screen in which a display screen and a touchpad are integrally formed, a contactless input interface using an optical sensor, an audio input interface, and/or the like. In the present disclosure, the input interface 130 does not necessarily have to include physical operation component parts such as the mouse and/or the keyboard. Possible examples of the input interface 130 include electrical signal processing circuitry configured to receive an electrical signal corresponding to an input operation from an external input device provided separately from the apparatus and to output the received electrical signal to the control circuit.

The display 140 is connected to the processing circuitry 150 and is configured to display various types of information and various types of image data output from the processing circuitry 150. For example, the display 140 is realized by using a liquid crystal monitor, a Cathode Ray Tube (CRT) monitor, a touch panel, or the like.

The processing circuitry 150 is configured to control constituent elements of the medical image processing apparatus 100 in accordance with the input operations received from the operator via the input interface 130. For example, the processing circuitry 150 is configured to store the image data output from the NW interface 110 into the storage 120. Further, for example, the processing circuitry 150 is configured to read the image data from the storage 120 and to have the image data displayed on the display 140. For example, the processing circuitry 150 is realized by using a processor.

An overall configuration of the medical image processing apparatus 100 according to the present embodiment has thus been explained. The medical image processing apparatus 100 according to the present embodiment structured as described above has a function of simulating heart surgery, by using the image data acquired by the medical image diagnosis apparatus 300.

For instance, as an example of techniques for simulating the heart surgery as described above, a technique is known by which, before surgery to open the chest, an optimal suture position is simulated for the surgery to join a heart valve and a valve base part with a graft (an artificial blood vessel). However, none of the conventional techniques take into account the deformations of the heart caused by opening and closing the chest. Accordingly, there are some situations where it is difficult to properly assist the surgery performed on the heart.

For example, the David procedure is known as surgery to keep the patient's valve to treat patients having aortic valve insufficiency. In the David procedure, the position in which the valve and the valve base part are sewed to a graft is determined by a medical doctor while the chest is open. Further, with the David procedure, until the chest is closed it is impossible to know the location to which the position sewed during the surgery will move after the chest is closed. For this reason, although the David procedure assures durability of the valve and can also achieve high Quality of Life (QOL) because the patient does not need to take an anticoagulant agent, implementation is sometimes avoided due to difficulty of the surgery.

To cope with the circumstances described above, the medical image processing apparatus 100 according to the present embodiment is configured to be able to properly assist the surgery performed on the heart. In the following sections, details of the medical image processing apparatus 100 with this configuration will be explained. As an example of the surgery performed on the heart, an example will be explained in which surgery on the aortic valve is simulated.

More specifically, the processing circuitry 150 includes an obtaining function 151, an estimating function 152, and an output function 153. The obtaining function 151 is an example of the obtaining unit. The estimating function 152 is an example of the estimating unit. The output function 153 is an example of the output unit.

The obtaining function 151 is configured to obtain feature values related to the shape and properties of the heart.

In this situation, the obtaining function 151 is configured to obtain the feature values from at least one of: an X-ray CT apparatus, an MRI apparatus, an ultrasound diagnosis apparatus, and a database. Further, as the feature values, the obtaining function 151 is configured to obtain at least one of: shape data of the heart, firmness of the heart, pressure of the heart, and the mass of the heart. In this situation, the shape data does not necessarily have to be volume data of a morphological image obtained by an X-ray CT apparatus or the like, but may be surface data recording a spatial distribution of surface positions of a tissue of the heart. Further, the "heart" subject to the obtaining process of the obtaining function 151 includes not only the ventricles, the atria, and the heart valves of the heart, but also one or more blood vessels such as the aorta and the coronary arteries connected to the ventricles, the atria, and the heart valves. The embodiment will be explained by using an example in which CT volume data rendering one or more of the ventricles, the atria, the heart valves, the coronary arteries, and the aorta is obtained from an X-ray CT apparatus, as the shape data of the heart.

First, the obtaining function 151 obtains the feature values related to the shape of the heart.

For example, via the NW interface 110, the obtaining function 151 obtains a CT image acquired by an X-ray CT apparatus or an MR image acquired by an MRI apparatus and obtains volume data rendering a part of the heart, a part of the aorta, and the aortic valve, from the obtained image.

A boundary condition is set with the boundary of the obtained volume data. For example, the obtaining function 151 obtains volume data of the region on the inside of a range in which the heart adheres to other sites in the patient's body and regards the region as a fixed end. Alternatively, the obtaining function 151 obtains volume data of a region fixed during the surgery and regards the region as a fixed end. The region obtained in this situation will serve as a region subject to a simulation.

Figure 2:
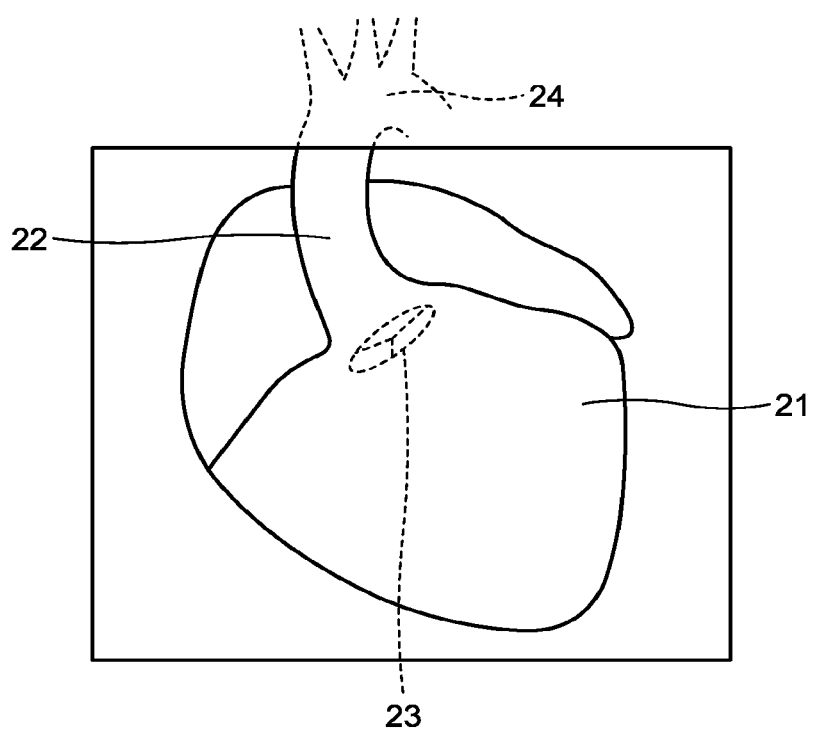
FIG. 2 is a drawing illustrating an example of a feature value obtaining process performed by an obtaining function according to the present embodiment.

FIG. 2 is a drawing illustrating an example of the feature value obtaining process performed by the obtaining function 151 according to the present embodiment.

For example, as illustrated in FIG. 2, from the CT image, the MR image, or the like, the obtaining function 151 obtains volume data rendering the heart 21, a part of the aorta 22, and the aortic valve 23. In this situation, as for the aorta 22, the obtaining function 151 obtains the range up to just before the part fixed to the aortic arch 24.

Further, the obtaining function 151 obtains the shape (including the dimension) of the graft from a catalog value or the like stored in advance in the storage 120 or from actually measuring the graft.

In this situation, the obtaining function 151 may further obtain volume data of parts of the vena cava, the pulmonary artery, and the pulmonary vein. As a result, it is possible to perform simulations more accurately.

Subsequently, the obtaining function 151 obtains feature values related to the properties of the heart.

For example, via the NW interface 110, the obtaining function 151 obtains an ultrasound image acquired by an ultrasound diagnosis apparatus and obtains information about firmness of the heart, firmness of blood vessels such as the aorta, and firmness of the heart valve, from the obtained image. Alternatively, the obtaining function 151 may obtain information about firmness of the heart, firmness of blood vessels such as the aorta, and firmness of the heart valve, from a database or the like stored in advance in the storage 120.

In this situation, as for the firmness, biological tissues may be regarded as elastic bodies or may be regarded as hyperelastic bodies. Further, it is also acceptable to regard biological tissues as anisotropic bodies while taking anisotropicity of myocardial fibers and blood vessels into account on the basis of a database or the like stored in advance.

After that, via the input interface 130, the obtaining function 151 receives, from the operator, an operation to designate a region to be used during the surgery as a fixed end, a simple support, or a moving boundary, i.e., a region in which it is possible to apply a condition to the magnitude and the orientation of a displacement or to a chronological history thereof during simulations. In the following sections, a region serving as the fixed end will be referred to as a Neumann condition region. A region serving as the simple support will be referred to as a Dirichlet condition region.

For example, the regions designated by the operator include a region serving as a boundary because of a surgical tool, a region serving as a boundary due to a restraint from an organ, and the like. When a region serves as a boundary because of a surgical tool, the boundary may be formed after a biological tissue is deformed by pulling an organ with a surgical tool or the like. In that situation, after a deformation simulation is performed with the moving of the region, a Neumann condition or a Dirichlet condition will be applied.

In this situation, the deformation amount of the biological tissue caused by pulling the organ with the surgical tool or the like, for example, may uniquely be determined by the operator on a screen displayed on the display 140, or results from a plurality of deformation amounts may be obtained. Alternatively, a plurality of deformation amounts may automatically be presented, so that the operator selects one of the presented deformation amounts. In that situation, for example, as the plurality of deformation amounts serving as the selection candidates, deformation amounts in surgery performed in the past or some combinations of such deformation amounts may be presented.

Subsequently, the obtaining function 151 obtains physical quantities related to the heart.

For example, from an examination result of a catheter examination, a database stored in advance in the storage 120, or the like, the obtaining function 151 obtains aortic pressure and left ventricular pressure. Further, from an ultrasound image obtained via the NW interface 110 or a database or a catalog value stored in advance in the storage 120, the obtaining function 151 obtains the mass of the heart, the mass of the blood vessels, the mass of the blood filling the blood vessels, and the mass of the graft.

The order in which the obtaining function 151 obtains the feature values related to the shape of the heart, the feature values related to the properties of the heart, and the physical quantities related to the heart may be changed as appropriate.

Returning to the description of FIG. 1, the estimating function 152 is configured to estimate the state of the heart after the chest is opened and after the chest is closed, by using the feature values obtained by the obtaining function 151.

In this situation, while taking into account a positional change of the heart caused by the opening and the closing of the chest, the estimating function 152 estimates the state of the heart after being deformed due to the positional change.

First, the estimating function 152 estimates the state of the heart after the chest is opened.

In actual surgery, a preparation is made before a treatment manipulation. Manipulations corresponding to the preparation include a manipulation to open the chest and a manipulation to deform the valve base part by approximately 90 degrees so that the aortic valve is visible to the practitioner. Accordingly, the estimating function 152 simulates the deformations caused by these two manipulations. In this situation, to simulate the deformations, it is necessary to determine: (1) incision regions of the chest and the aorta, (2) the angle by which the chest is opened, and (3) the moving position of the aorta.

In this situation, as for the incision regions of the chest and the aorta, from where to where the chest is to be incised and in which position the aorta is to be incised, for example, may uniquely be determined by the operator on a screen displayed on the display 140, or results from a plurality of incision regions may be obtained. Alternatively, a plurality of incision regions may automatically be presented so that the operator selects one of the incision regions. In that situation, for example, as the plurality of incision regions serving as the selection candidates, incision regions in surgery performed in the past or some combinations of such incision regions may be presented.

Further, the angle by which the chest is to be opened, for example, may uniquely be determined by the operator on a screen displayed on the display 140, or results from a plurality of angles may be obtained. Alternatively, a plurality of angles may automatically be presented so that the operator selects one of the angles. In that situation, for example, as the plurality of angles serving as the selection candidates, angles in surgery performed in the past or some combinations of such angles may be presented.

Figure 3:
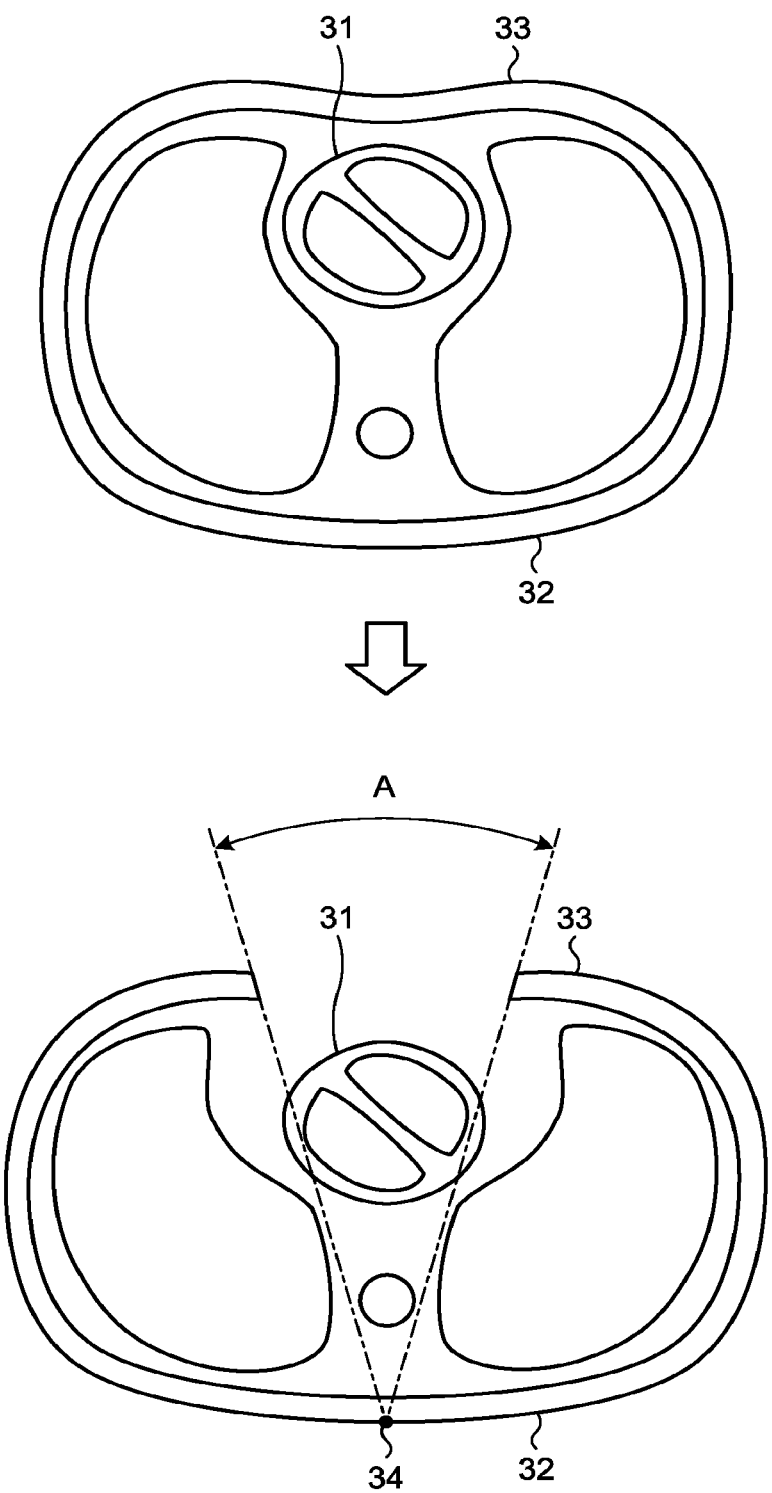
FIG. 3 is a drawing illustrating an example of an open chest angle setting process performed by an estimating function according to the present embodiment.

FIG. 3 is a drawing illustrating an example of an open chest angle setting process performed by the estimating function 152 according to the present embodiment. In the present example, FIG. 3 illustrates a cross-sectional plane of the chest orthogonal to the body axis of the examined subject (the patient) and conceptually illustrates the cross-sectional plane in a position including the heart 31.

For example, as illustrated in FIG. 3, the estimating function 152 determines, as the angle by which the chest is to be opened, an angle A spreading in the left-and-right directions on the chest side 33 while being centered on a point 34 set at the center on the dorsal side 32 of the chest.

Further, in the actual surgery, a part of the biological tissue moves as a result of the chest being opened, and also, the direction of a load from the gravity changes. Accordingly, the estimating function 152 simulates a deformation caused by the forces applied to the heart and the blood vessels by the move and the change.

In this situation, as for the moving position of the aorta, the location to which the opening of the aorta should be moved, for example, may uniquely be determined by the operator on a screen displayed on the display 140, or results from a plurality of moving positions may be obtained. Alternatively, a plurality of moving positions may automatically be presented, so that the operator selects one of the moving positions. In that situation, for example, as the plurality moving positions serving as the selection candidates, moving positions in surgery performed in the past or some combinations of such moving positions may be presented.

Further, in the actual surgery, as a result of moving the aorta, the direction of a load from the gravity changes. Accordingly, the estimating function 152 simulates a deformation caused by the forces applied to the heart and the blood vessels by the move and the change.

Subsequently, the estimating function 152 stores, into the storage 120, volume data indicating the state of the heart (including the aorta, the aortic valve, and the like) after the chest is opened, obtained from the abovementioned simulations. In this situation, for example, the estimating function 152 may save, in the storage 120, the incision regions of the chest and the aorta, the angle by which the chest is to be opened, and the moving position of the aorta that were determined in the simulations, so that the information can be used in a simulation of the state after the chest is closed (explained later).

When performing the simulations of the state after the chest is opened as described above, the estimating function 152 may estimate the state of the heart after deformations, by further taking into account at least one of: the heart being pressured by other structures, an inflow of blood into the heart and blood vessels, cardiac beats of the heart, relaxation of muscles caused by anesthesia, and temperature.

For example, as for the heart being pressured by other structures, the estimating function 152 estimates the state of the heart after deformations, by taking into account, the heart being pressured by the lungs due to a cardiopulmonary arrest or resuscitation, attachment and detachment of an artificial cardiopulmonary device or the like, as well as the heart being pressured by the pericardium, and the like. Further, for example, as for the inflow of blood into the heart and the blood vessels, the estimating function 152 estimates the state of the heart after deformations by taking into account the deformations of the blood vessels and the heart caused by an increase or a decrease in the blood pressure due to the inflow and an outflow of blood.

Further, for example, as for the cardiac beats of the heart, the estimating function 152 estimates the state of the heart after deformations by taking into account the deformations of the heart and the blood vessels caused by contraction of the myocardia in conjunction with the cardiac beats. Further, for example, as for the relaxation of the muscles caused by anesthesia, the estimating function 152 estimates the state of the heart after deformations by taking into account, for example, changes in tension caused by the whole body being relaxed due to the anesthesia. Further, for example, as for the temperature, the estimating function 152 estimates the state of the heart after deformations, by taking into account expansions and contractions of biological tissues and the graft due to changes in the temperature.

Figure 5:
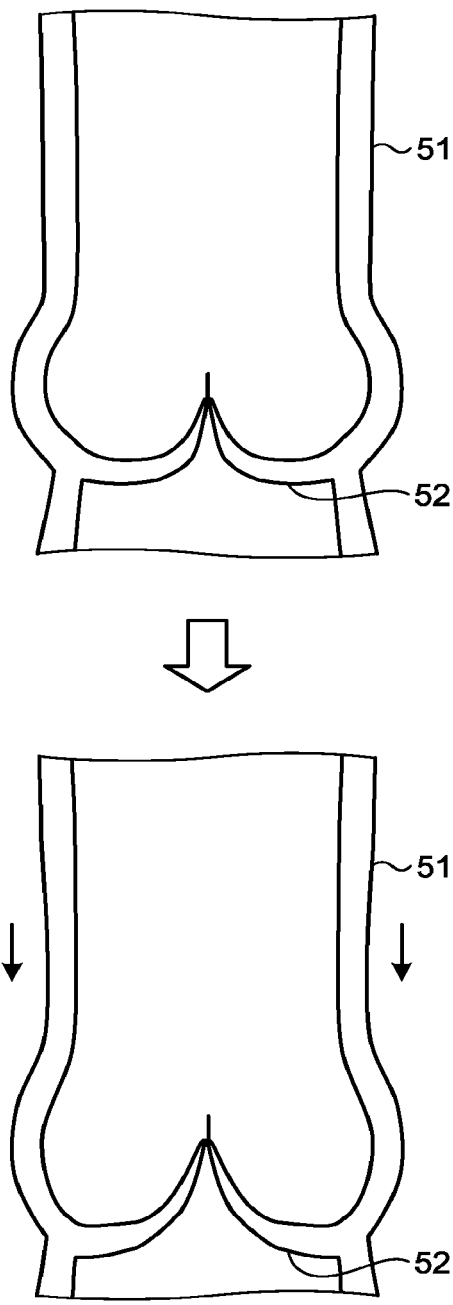
FIG. 5 is a drawing illustrating another example of the simulation of the state after the chest is opened that is performed by the estimating function according to the present embodiment.

FIGS. 4 and 5 are drawings illustrating examples of the simulations of the state after the chest is opened that is performed by the estimating function 152 according to the present embodiment. FIGS. 4 and 5 each conceptually illustrate cross-sectional planes of a part of the aorta 41 and the aortic valve 42. The top sections of the drawings illustrate the state before the chest is opened, whereas the bottom sections of the drawings illustrate the state after the chest is opened.

For example, as illustrated in FIG. 4, while the chest is opened, the blood pressure in the aorta disappears due to an outflow of blood. Accordingly, the internal pressure of a region from the aorta 41 to the aortic valve 42 decreases, and as a result, the region from the aorta 41 to the aortic valve 42 is deformed into a deflated shape. Further, for example, as illustrated in FIG. 5, while the chest is opened, because the upward pressure from the diaphragm disappears, the region from the aorta 51 to the aortic valve 52 is deformed into a vertically-elongated shape. For example, the estimating function 152 estimates the state of the heart after deformations by taking these deformations into account.

Subsequently, the estimating function 152 estimates the state of the heart after treatment.

More specifically, the estimating function 152 simulates a deformation caused by a manipulation to recover functions of the aortic valve. In this situation, the estimating function 152 uses an existing technique for a treatment simulation, to obtain the shapes of the heart, the aorta, and the aortic valve after the treatment.

To be performed in the actual surgery are (1) a manipulation to incise the valve base part to have a goal shape, i.e., a three-peak shape having peaks at three points of commissures where the starting parts of two valve cusps positioned adjacent to each other in the aortic valve are joined with each other; and (2) a manipulation to sew the valve base part and the graft together. Accordingly, the estimating function 152 simulates the deformations to be caused by the two manipulations.

In this situation, the estimating function 152 reads the volume data indicating the state of the heart after the chest is opened and being stored in the storage 120 and performs a simulation, while using the read volume data and the shape of the graft obtained by the obtaining function 151 as inputs.

Figure 6:
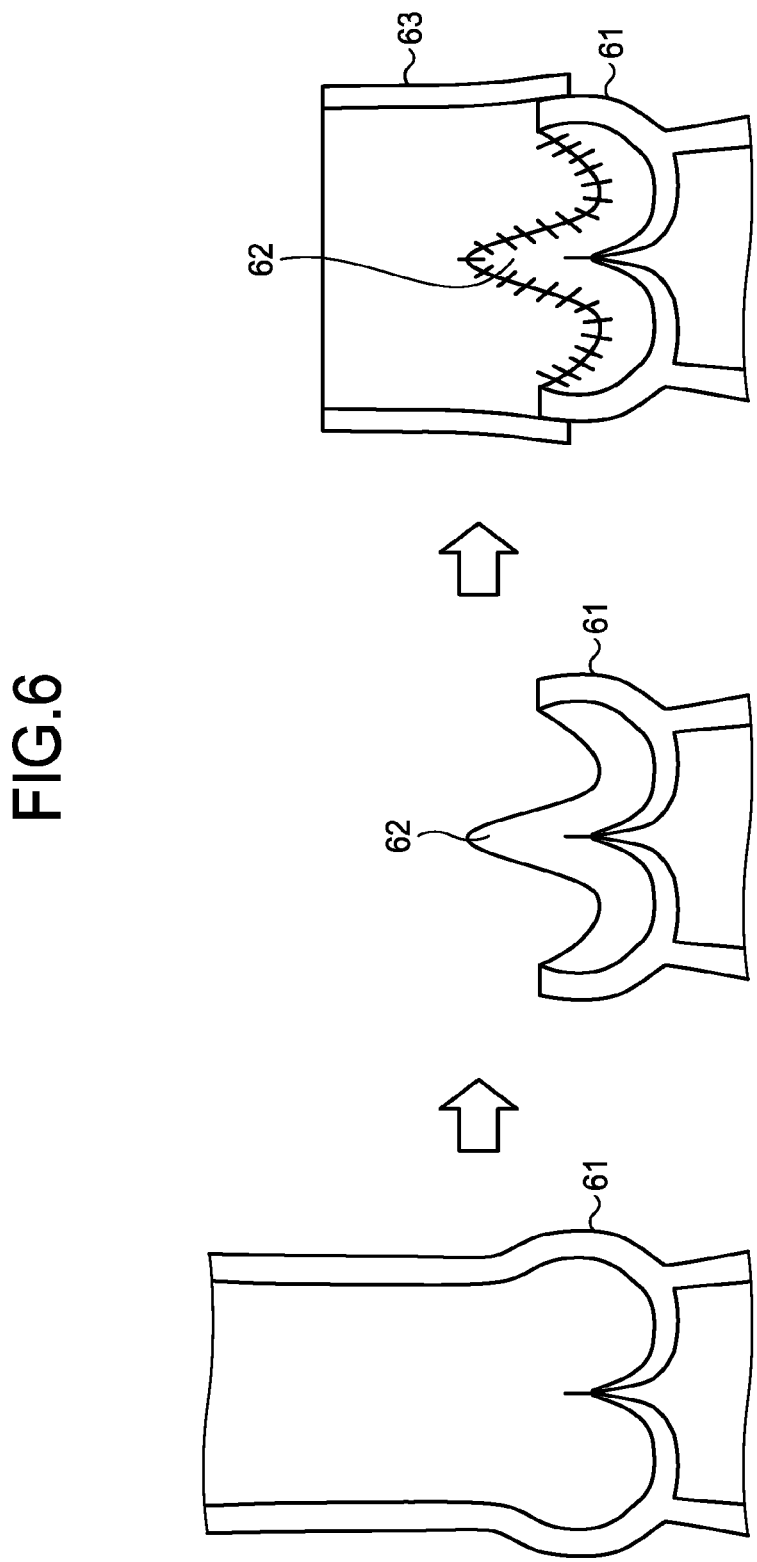
FIG. 6 is a drawing illustrating an example of a simulation of a manipulation to recover functions of an aortic valve performed by the estimating function according to the present embodiment.

FIG. 6 is a drawing illustrating an example of the simulation of the manipulation to recover the functions of the aortic valve performed by the estimating function 152 according to the present embodiment.

For example, as illustrated from the left to the middle sections of FIG. 6, the estimating function 152 simulates incising a valve base part 61 into a goal shape, i.e., the three-peak shape having the three commissures 62 as the peaks, by using an existing technique for simulating an incision of an organ.

Further, for example, as illustrated from the middle to the right sections of FIG. 6, the estimating function 152 simulates sewing and joining the valve base part 61 and a graft 63 together, by using an existing technique for simulating sewing an organ and an artificial object together. In this situation, the estimating function 152 sequentially simulates:

joining the commissures 62 of the valve base part 61 with the inner circumferential surface of the graft (the first row); and subsequently joining the valve base part 61 with the inner circumferential surface of the graft in a full circle (the second row).

After that, the estimating function 152 stores, into the storage 120, volume data indicating the state of the heart (including the aorta, the aortic valve, and the like) after the treatment that is obtained from the simulations described above.

Subsequently, the estimating function 152 estimates the state of the heart after the chest is closed.

More specifically, the estimating function 152 simulates deformations caused by a manipulation of joining the graft with the aorta while deforming the graft, the valve base part, and the heart and a manipulation of closing the chest.

In this situation, the estimating function 152 reads the volume data indicating the state of the heart after the treatment and being stored in the storage 120 and performs the simulation while using the read volume data and the shape of the graft obtained by the obtaining function 151 as inputs. In this situation, for example, the estimating function 152 may perform the simulation of the state after the chest is closed, by using the incision regions of the chest and the aorta, the angle by which the chest is opened, and the moving position of the aorta that were saved in the storage 120 when the simulation was performed of the state after the chest is opened. For example, the estimating function 152 may use the angle by which the chest is opened that is saved in the storage 120, as the angle by which the chest is closed.

Figure 7:
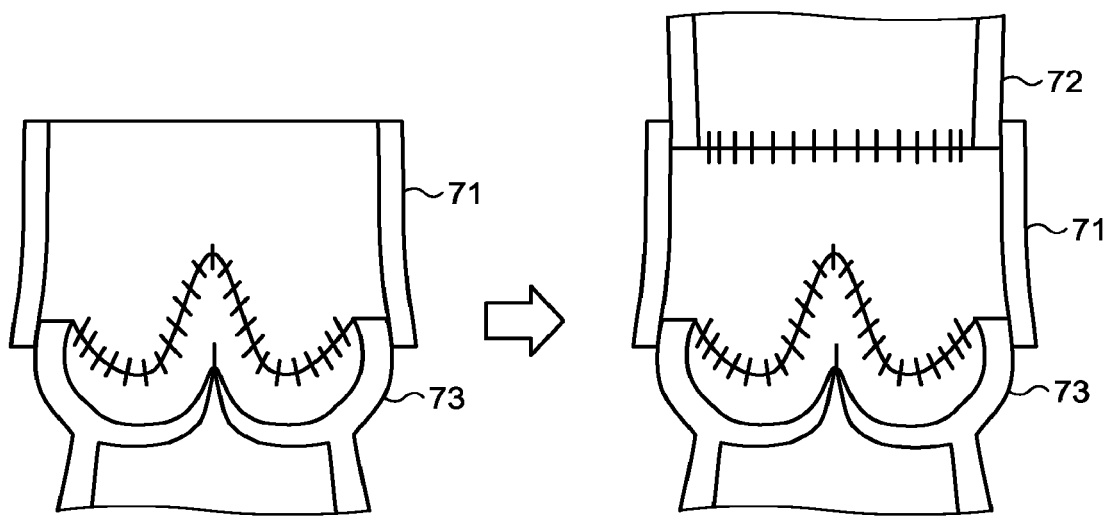
FIG. 7 is a drawing illustrating an example of a simulation of a manipulation to join a graft with the aortic valve performed by the estimating function according to the present embodiment.

FIG. 7 is a drawing illustrating an example of the simulation of the manipulation to join the graft with the aortic valve performed by the estimating function 152 according to the present embodiment.

For example, as illustrated from the left to the right sections of FIG. 7, the estimating function 152 simulates sewing and joining an opening part of a graft 71 with the patient's blood vessel 72 of the aorta, by using an existing technique for simulating sewing an organ and an artificial object together. In this situation, the estimating function 152 deforms the graft 71, a valve base part 73, and the heart so that the opening part of the graft 71 and the patient's blood vessel 72 are joined with each other. Further, in this situation, the estimating function 152 sets an angle and a position of the aorta after the chest is closed in such a manner that the position of the aorta before the chest is opened is proximate to the position of the aorta after the chest is closed.

After that, the estimating function 152 causes a deformation so as to join together the incised open chest. More specifically, the estimating function 152 obtains the two incised cross-sections of the chest and causes the deformation so that the incised cross-sections adhere to each other.

Subsequently, the estimating function 152 stores, into the storage 120, volume data indicating the state of the heart (including the aorta, the aortic valve, and the like) after the chest is closed that was obtained by the simulation described above.

In this situation, when simulating the state after the chest is closed as described above, the estimating function 152 may estimate, similarly to the simulation of the state after the chest is opened, the state of the heart after being deformed by further taking into account at least one of: the heart being pressured by other structures, an inflow of blood into the heart and blood vessels, cardiac beats of the heart, relaxation of muscles caused by anesthesia, and temperature.

Returning to the description of FIG. 1, the output function 153 outputs parameters related to the state of the heart estimated by the estimating function 152 to the display 140.

In this situation, as the parameters related to the state of the heart, the output function 153 outputs information indicating a treatment effect of the surgery to the display 140. More specifically, as the information indicating the treatment effect of the surgery, the output function 153 outputs, to the display 140, an effective height, a coaptation height, the coordinates of the center of a free edge of each of a plurality of valve cusps included in the heart valve, information indicating whether or not the positions of the centers of the free edges of the valve cusps match one another, and the like.

In this situation, the output function 153 reads the volume data indicating the state of the heart after the chest is closed and being stored in the storage 120 and calculates the parameters related to the state of the heart on the basis of the read volume data.

Figure 8:
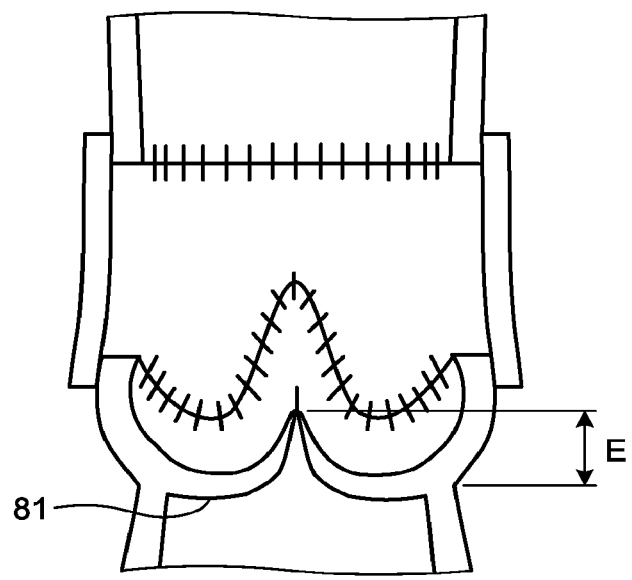
FIG. 8 is a drawing of an example of a process to output parameters related to the state of the heart performed by an output function according to the present embodiment.
Figure 9:
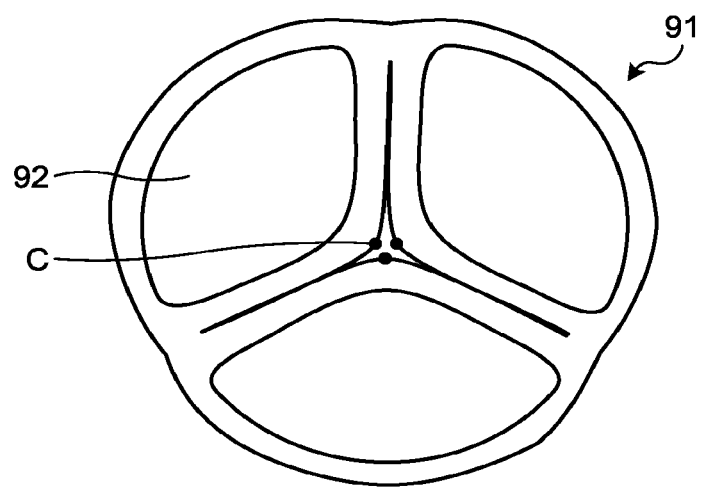
FIG. 9 is a drawing of another example of the process to output the parameters related to the state of the heart performed by the output function according to the present embodiment.

FIGS. 8 and 9 are drawings of examples of the process to output the parameters related to the state of the heart performed by the output function 153 according to the present embodiment.

For example, as illustrated in FIG. 8, the output function 153 calculates an effective height represented by a length E obtained by perpendicularly projecting the section of an aortic valve 81 from the root of the valve cusp to the tip end of the free edge of the valve cusp onto the blood vessel and further outputs the calculated effective height to the display 140.

Further, for example, as illustrated in FIG. 9, the output function 153 outputs the coordinates of the center C of the free edge of each of three valve cusps 92 included in the aortic valve 91, to the display 140. In this situation, the output function 153 obtains the coordinates of the center C of the free edge by equally halving the length of the free edge of each of the valve cusps 92. In this situation, the origin of the coordinates and the coordinate axes are arbitrary. Further, the output function 153 outputs, to the display 140, information indicating whether or not the positions of the centers C of the free edges of the three valve cusps 92 included in the aortic valve 91 match one another, and if the positions do not match, how much deviation there is.

For example, when the diameter of the graft is too large, there may be some situations where the effective height is not sufficiently large or where the positions of the centers of the free edges of the valve cusps do not match one another. Accordingly, it is effective to output the abovementioned information as a treatment effect of the surgery.

Processing functions of the processing circuitry 150 have thus been explained. For example, when the processing circuitry 150 is realized by using a processor, the processing functions described above are stored in the storage 120 in the form of computer-executable programs. In that situation, the processing circuitry 150 is configured to realize the functions corresponding to the programs by reading and executing the programs from the storage 120. In other words, the processing circuitry 150 that has read the programs has the processing functions indicated within the processing circuitry 150 in FIG. 1.

Further, it is also acceptable to structure the processing circuitry 150 by combining together a plurality of independent processors, so that the processing functions are realized as a result of the processors executing the programs. Further, the processing functions of the processing circuitry 150 may be realized as being distributed among or integrated into one or more pieces of processing circuitry, as appropriate. Further, the processing functions of the processing circuitry 150 may be realized with a mixture of hardware such circuits and software.

Further, although the example is explained above in which the single piece of storage (i.e., the storage 120) stores therein the programs corresponding to the processing functions, possible embodiments are not limited to this example. For instance, a plurality of pieces of storage may be arranged in a distributed manner, so that the processing circuitry 150 reads and executes corresponding programs from the individual pieces of storage.

Figure 10:
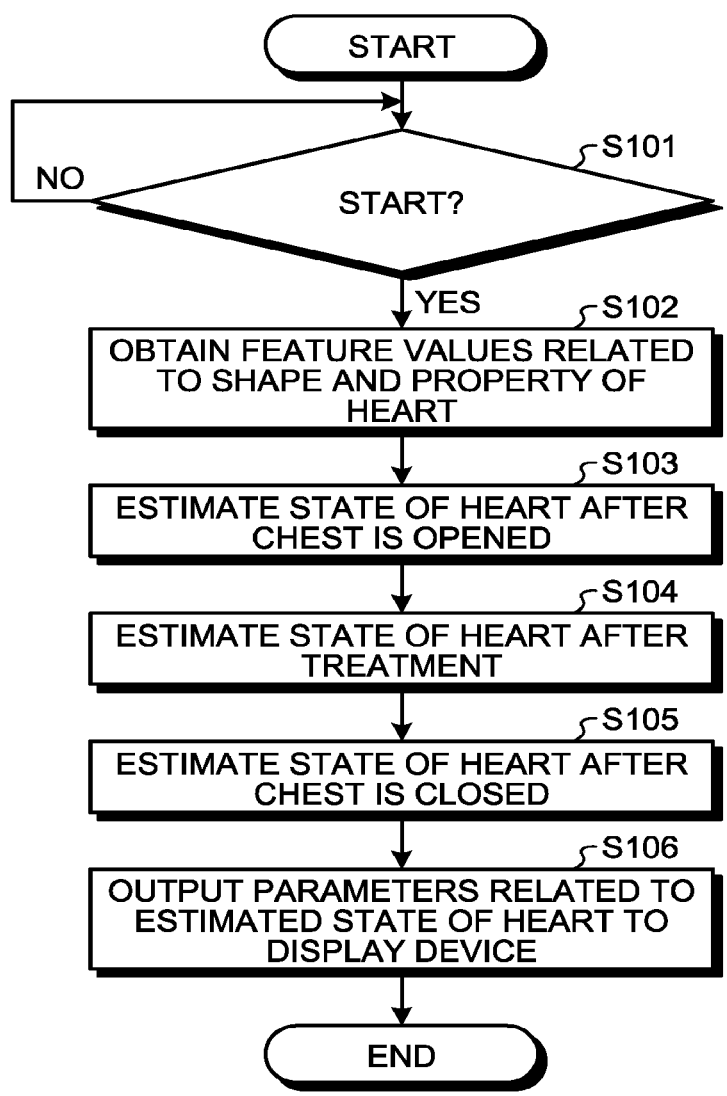
FIG. 10 is a flowchart illustrating a processing procedure in a process performed by the medical image processing apparatus according to the present embodiment.

FIG. 10 is a flowchart illustrating a processing procedure in a process performed by the medical image processing apparatus 100 according to the present embodiment.

For example, as illustrated in FIG. 10, in the present embodiment, when an instruction to start a simulation is received from the operator via the input interface 130 (step S101: Yes), the obtaining function 151 obtains feature values related to the shape and the properties of the heart (step S102). In this situation, the obtaining function 151 obtains volume data rendering the heart, a part of the aorta, and the aortic valve.

After that, the estimating function 152 estimates the state of the heart after the chest is opened, by using the feature values obtained by the estimating function 152 (step S103). As a result, the estimating function 152 stores, into the storage 120, volume data indicating the state of the heart (including the aorta, the aortic valve, and the like) after the chest is opened.

Further, the estimating function 152 reads the volume data indicating the state of the heart after the chest is opened from the storage 120 and estimates the state of the heart after the treatment, on the basis of the read volume data (step S104). As a result, the estimating function 152 stores, into the storage 120, volume data indicating the state of the heart (including the aorta, the aortic valve, and the like) after the treatment.

Further, the estimating function 152 reads the volume data indicating the state of the heart after the treatment from the storage 120 and estimates the state of the heart after the chest is closed, on the basis of the read volume data (step S105). As a result, the estimating function 152 stores, into the storage 120, volume data indicating the state of the heart (including the aorta, the aortic valve, and the like) after the chest is closed.

Subsequently, the output function 153 reads the volume data indicating the state of the heart after the chest is closed from the storage 120 and outputs, to the display 140, parameters related to the state of the heart estimated by the estimating function 152, on the basis of the read volume data (step S106).

In this situation, the processes at steps S101 and S102 described above are realized, for example, as a result of the processing circuitry 150 invoking and executing a predetermined program corresponding to the obtaining function 151 from the storage 120. Further, the processes at steps S103 through S105 are realized, for example, as a result of the processing circuitry 150 invoking and executing a predetermined program corresponding to the estimating function 152 from the storage 120. Further, the process at step S106 is realized, for example, as a result of the processing circuitry 150 invoking and executing a predetermined program corresponding to the output function 153 from the storage 120.

As explained above, in the present embodiment, because the optimal position to sew the valve and the valve base part to the graft is calculated before the surgery or before the chest is closed, through the simulation of the chest opening process and the chest closing process, it is possible to assist the surgery performed on the aortic valve by making it possible to proactively select the David procedure (the surgery to keep the patient's valves) even for medical cases where artificial valve surgery would conventionally be performed. Accordingly, it is possible to enhance QOL of the patient.

As explained above, according to at least one aspect of the present embodiments, it is possible to assist the surgery performed on the heart more properly.

In the embodiments above, the example of simulating the surgery performed on the aortic valve is explained. However, the simulation method described above is similarly applicable to surgery performed on other sites of the heart.

The term "processor" used in the description of the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in the storage, it is also acceptable to directly incorporate the programs in the circuits of the processors. In that situation, the processors realize the functions by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof.

The programs executed by the processors are provided as incorporated in advance in a Read-Only Memory (ROM), storage, or the like. The programs may be provided as being recorded on a non-transitory computer-readable storage medium such as a Compact Disk Read-Only Memory (CD-ROM), a Flexible Disk (FD), a Compact Disk Recordable (CD-R), or a Digital Versatile Disk (DVD), in a file that is in an installable or executable format for the devices. Further, the programs may be stored in a computer connected to a network such as the Internet so as to be provided or distributed as being downloaded via the network. For example, the programs are structured as modules including the processing functions described above. In actual hardware, as a result of a CPU reading and executing the programs from a storage medium such as a ROM, the modules are loaded into a main storage device so as to be generated in the main storage device.

According to at least one aspect of the embodiments described above, it is possible to assist the surgery performed on the heart more properly.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to
obtain feature values related to a shape and a property of a heart of a subject;

estimate, by using the feature values, a first shape of the heart after being deformed by a manipulation to open a chest of the subject;

estimate, based on the first shape of the heart, a second shape of the heart after being deformed by a manipulation to close the chest after a treatment of a heart valve is completed; and output a parameter related to the second shape of the heart to a display.

2. The medical image processing apparatus according to claim 1, wherein the processing circuitry obtains the feature values from at least one of: an X-ray CT apparatus, a magnetic resonance imaging apparatus, an ultrasound diagnosis apparatus, and a database.

3. The medical image processing apparatus according to claim 1, wherein, as the feature values, the processing circuitry obtains at least one of: shape data of the heart, firmness of the heart, pressure of the heart, and mass of the heart.

4. The medical image processing apparatus according to claim 1, wherein the processing circuitry takes into account a positional change of the heart caused by the manipulation to open the chest and the manipulation to close the chest and estimates the first shape and the second shape of the heart.

5. The medical image processing apparatus according to claim 4, wherein the processing circuitry estimates the first shape and the second shape of the heart, while further taking into account at least one of: the heart being pressured by another structure; an inflow of blood into the heart and a blood vessel; cardiac beats of the heart; relaxation of a muscle caused by anesthesia; and temperature.

6. The medical image processing apparatus according to claim 1, wherein, as the parameter, the processing circuitry outputs information indicating a treatment effect of surgery to the display.

7. The medical image processing apparatus according to claim 6, wherein, as the information indicating the treatment effect, the processing circuitry outputs, to the display, at least one of: an effective height, a coaptation height, coordinates of a center of a free edge of each of a plurality of valve cusps included in a heart valve, and information indicating whether positions of the centers of the free edges of the valve cusps match one another and how much deviation there is.

8. The medical image processing apparatus according to claim 1, wherein the processing circuitry obtains the feature values with respect to a range of the heart including ventricles, atria, heart valves, and a part of an aorta.

9. The medical image processing apparatus according to claim 1, wherein the processing circuitry obtains the feature values related to the shape, based on an image of the heart generated before the chest is opened.

10. The medical image processing apparatus according to claim 1, wherein the processing circuitry estimates the first shape of the heart, according to an incision region of the chest and an aorta, an angle by which the chest is opened, and a moving position of the aorta.

11. The medical image processing apparatus according to claim 1, wherein the processing circuitry:

estimates the first shape of the heart after the chest is opened, based on a deformation simulation of a biological tissue; and estimates the second shape of the heart, by a treatment simulation based on the first shape of the heart and a deformation simulation of a biological tissue after the treatment.

12. The medical image processing apparatus according to claim 11, wherein the deformation simulation of the biological tissue after the treatment estimates the state of the heart, based on at least a deformation amount of the biological tissue after the treatment and a physical quantity of a graft for the treatment.

13. A medical image processing method, comprising:

obtaining feature values related to a shape and a property of a heart of a subject;

estimating, by using the feature values, a first shape of the heart after being deformed by a manipulation to open a chest of the subject;

estimating, based on the first shape of the heart, a second shape of the heart after being deformed by a manipulation to close the chest after a treatment of a heart valve is completed; and outputting a parameter related to the second shape of the heart to a display.

14. A non-transitory computer-readable storage medium having plural computer-executable commands recorded therein, the commands causing the computer to realize:

an obtaining function to obtain feature values related to a shape and a property of a heart of a subject;

an estimating function to estimate, by using the feature values, a first shape of the heart after being deformed by a manipulation to open a chest of the subject and estimate, based on the first shape of the heart, a second shape of the heart after being deformed by a manipulation to close the chest after a treatment of a heart valve is completed; and an output function to output a parameter related to the second shape of the heart to a display.

* * * * *